United States Patent
Love et al.

(10) Patent No.: US 6,436,368 B1
(45) Date of Patent: Aug. 20, 2002

(54) PROCESS FOR PREPARING BECLOMETHASONE DIPROPIONATE FREON® CLATHRATE

(75) Inventors: George M. Love, Mountainside; Stanley Rosenhouse, Westfield, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/690,388

(22) Filed: Oct. 17, 2000

Related U.S. Application Data

(63) Continuation of application No. 08/287,576, filed on Aug. 9, 1994, now abandoned.

(51) Int. Cl.[7] .............................. C07C 7/13; A61L 9/04; A61K 31/56; B01D 3/12; B01D 5/00
(52) U.S. Cl. ........................... 424/46; 424/45; 514/180; 95/190; 95/902; 210/610; 570/134
(58) Field of Search .................... 528/210; 424/243, 424/46, 45; 95/190, 902; 570/134; 210/610; 514/180

(56) References Cited

U.S. PATENT DOCUMENTS

| | | | | |
|---|---|---|---|---|
| 4,044,126 A | * | 8/1977 | Cook et al. | 424/243 |
| 4,364,923 A | | 12/1982 | Cook et al. | 424/46 |
| 4,414,209 A | | 11/1983 | Cook et al. | 424/243 |
| 4,864,012 A | * | 9/1989 | Britt | 528/210 |

OTHER PUBLICATIONS

"Davison Molecular Sieves," product brochure published by W.R. Grace & Co., date unknown.
"UOP Molecular Sieves," product brochure published by UOP, Inc., date unknown.
"Molecular Sieve Type 4A Data Sheet," product information published by Chemical Dynamics Corp., So. Plainfield, New Jersey, date unknown.

* cited by examiner

*Primary Examiner*—Frederick Krass
*Assistant Examiner*—Clinton Ostrup
(74) *Attorney, Agent, or Firm*—Paul A. Thompson; Robert A. Franks

(57) ABSTRACT

Described is a process for preparing beclomethsaone dipropionate Freon® clathrate comprising the use of an agent which selectively binds methanol to selectively remove methanol from a mixture of methanol and Freon® 11 containing beclomethasone dipropionate.

8 Claims, No Drawings

US 6,436,368 B1

PROCESS FOR PREPARING BECLOMETHASONE DIPROPIONATE FREON® CLATHRATE

CROSS-REFERENCE TO RELATED APPLICATIONS

This application is a continuation of Ser. No. 08/287,576 filed Aug. 9, 1994 now abandoned.

This invention relates to an improved process for producing the Freon® clathrate of beclomethasone dipropionate.

BACKGROUND

Beclomethasone dipropionate is a commercially important corticosteroid used for the treatment of asthma and allergic rhinitis. It is often administered in the form of an inhaler containing beclomethasone dipropionate as a trichloromonofluoromethane (Freon® 11) clathrate as described in U.S. Pat. Nos. 4,044,126, 4,414,209 and 4,364,923.

Processes for preparing the Freon® 11 clathrate of beclomethasone dipropionate are described in U.S. Pat. Nos. 154,044,126, 4,414,209 and 4,364,923. The currently preferred process involves adding a solution of beclomethasone dipropionate in hot methanol to a large volume of Freon® 11. The methanol is then removed by azeotropic distillation.

The current process is inefficient, requiring the use of large volumes (e.g. 218 kg) of Freon® 11 per kg of beclomethasone diproprionate because the methanol/Freon® 11 azeotrope only contains about 2% methanol. The use of large volumes of Freon® 11 is undesirable due to the rapidly escalating cost of such chlorofluorocarbons. In addition, there are significant environmental concerns surrounding the use of Freon®. The development of a process which would not require large volumes of Freon® 11 is therefore highly desirable.

The ability of certain molecular sieves to bind methanol is known in the art. The use of molecular sieves to remove a solute which is a small polar molecule, such as water or methanol, from a solution is described in U.S. Pat. No. 4,864,012. The use of molecular sieves to remove water from Freon® refrigerants is also known.

Silica gel is a colloidal form of silica known in the art as a dessicant, and as an adsorbent used as the stationary phase in chromatographic separations.

SUMMARY OF THE INVENTION

The present invention provides a process for preparing beclomethasone dipropionate Freon® 11 clathrate using low volumes of Freon® 11.

The present invention provides a process for forming the beclomethasone dipropionate Freon® 11 clathrate comprising the use of an agent which selectively binds methanol to selectively remove methanol from a mixture of methanol and Freon® 11 containing beclomethasone dipropionate.

More particularly, the present invention comprises combining a solution of beclomethasone dipropionate in hot methanol with Freon® 11, heating the mixture to reflux temperature to generate a vapor, contacting the vapor with an agent which selectively binds methanol, condensing the vapor and returning the condensed vapor to the mixture. Alternatively, the present invention comprises combining a solution of beclomethasone dipropionate in hot methanol with Freon® 11, heating the mixture to reflux temperature to generate a vapor, condensing the vapor, contacting the condensed vapor with an agent which selectively binds methanol, and returning the condensed vapor to the mixture.

Preferably the methanol binding agent is molecular sieves, and more preferably type 3A, type 4A or type 5A sieves.

In a particularly preferred embodiment, the instant process utilizes about 4 L of methanol, about 7.5 L of Freon® 11 and about 32 kg of molecular sieves per kg of beclomethasone dipropionate.

After use the molecular sieves can be regenerated, by heating to 1500° to 200° C. to desorb the bound methanol. Regenerated sieves can be subsequently reused in the process of the present invention.

The Freon® 11 can also be distilled and reused in the process of the present invention. In addition, the process of the present invention can be carried out in an essentially closed system thereby preventing the release of Freon® to the environment.

DETAILED DESCRIPTION

As used herein the term "methanol binding agent" means a solid reagent that selectively and irreversibly binds the methanol in a methanol/Freon® mixture. A preferred methanol binding agent is molecular sieves, and more preferably type 3A, type 4A or type 5A sieves. Another preferred methanol binding agent is silica gel. "Irreversible binding" means that the methanol remains bound to the binding agent until subjected to suitable conditions to effect its release. In the case of molecular sieves, methanol remains bound to the sieves until subjected to heating to high temperature, e.g. 1500° to 2000° C.

The use of methanol to dissolve the beclomethasone dipropionate is necessary due to the relative insolubility of the steroid in Freon® 11. The beclomethasone dipropionate remains at least partially soluble in the mixture formed by combination of the methanol solution with the Freon® 11. Removal of the methanol solvent from the beclomethasone dipropionate/methanol/Freon® 11 mixture serves to drive the crystallization of beclomethasone dipropionate from solution in the form of the Freon® 11 clathrate.

To carry out the process of the present invention, dissolve beclomethasone dipropionate in a minimal amount of hot methanol, preferably utilizing about 4 mL methanol per gram of steroid. Add the hot solution to a suitable volume of chilled Freon® 11, preferably 7 mL to 8 mL of Freon® per gram of steroid, and most preferably about 7.5 mL of Freon® per gram. Heat the stirred mixture to reflux temperature to generate a vapor which is a Freon® 11 methanol azeotrope. Contact the vapor with a methanol binding agent, preferably silica gel or molecular sieves, more preferably molecular seives, and most preferably type 3A, type 4A or type 5A sieves, then condense the vapor and return the condensed vapor to the mixture. Reflux the mixture for about 4 hours or until substantially all of the methanol has been removed (e.g. until less than 2% methanol remains in the mixture). Cool the mixture and filter to collect the solid Freon® clathrate.

In an alternative embodiment, generate the vapor as described above, condense the vapor, contact the condensed vapor with a methanol binding agent, preferably silica gel or molecular sieves, more preferably molecular sieves, and most preferably type 3A, type 4A or type 5A sieves, then return the condensed vapor to the mixture. Continue refluxing until substantially all of the methanol is removed, as described above, and collect the Freon® clathrate by filtration.

The following examples illustrate the process of this invention:

EXAMPLE 1

Dissolve 0.5 kg of beclomethasone dipropionate in 2.0 L of refluxing methanol (MeOH). Add the hot solution to 3.75 L of Freon® 11 and stir the mixture. Heat the mixture at reflux (heating bath temperature 53°–58° C.) for 9 hours while passing the vapors through 16 kg of type 4A molecular sieves and returning the condensed vapor to the mixture. As the methanol is removed from the mixture, the beclomethasone dipropionate Freon® 11 clathrate precipitates from solution. After the methanol is removed, filter to collect the clathrate precipitate and wash twice with Freon® 11. Dry the solid with a stream of nitrogen to give 0.586 kg (quantitative yield) of beclomethasone dipropionate Freon® 11 clathrate. Analysis of the product shows 0.01% MeOH by weight.

Following essentially the same procedure as described for Example 1 the following results were obtained:

| Example # | Reflux times (hours) | Bath Temp. (° C.) | MeOH remaining in M.L.* (wt %) | Yield of clathrate | % Freon in isolated clathrate |
|---|---|---|---|---|---|
| 1A | 9 | 38–44 | 7 | 525 g‡ | 18% |
| 1B | 11 | 41–44 | 1.7 | 586 g | 20% |
| 1C | 7 | 55–57 | 0.04 | 540 g† | 19% |

*Percentage by weight of methanol remaining in the mother liquor after collection of the beclomethasone dipropionate Freon ® clathrate.
‡Lower yield of clathrate due to elevated levels of methanol remaining in the mother liquor.
†Some clathrate product lost during work-up.

We claim:

1. A process for preparing beclomethasone dipropionate trichloromonofluoromethane clathrate comprising combining a beclomethasone dipropionate solution, formed using about 4 liters of hot methanol per kilogram of beclomethasone dipropionate, with about 7 to about 8 liters of trichloromonofluoromethane per kilogram of beclomethasone dipropionate to form a mixture, heating the mixture to reflux to generate a vapor, contacting the vapor with about 32 kilograms, per kilogram of beclomethasone dipropionate, of a methanol binding agent selected from the group consisting of silica gel or a molecular sieve, condensing the vapor and returning the condensed vapor to the mixture.

2. The process of claim 1 wherein the methanol binding agent is a gel or molecular sieve.

3. The process of claim 2 wherein the methanol binding agent is a type 3A, type 4A or type 5A molecular sieve.

4. The process of claim 1 wherein the methanol binding agent is a molecular sieve and the process further includes the step of regenerating the molecular sieve that has contacted vapor by heating said molecular sieve to 150° to 200° C. to remove adsorbed methanol.

5. A process for preparing beclomethasone dipropionate trichloromonofluoromethane clathrate comprising combining a beclomethasone dipropionate solution, formed using about 4 liters of hot methanol per kilogram of beclomethasone dipropionate, with about 7 to about 8 liters of trichloromonofluoromethane per kilogram of beclomethasone dipropionate to form a mixture, heating the mixture to reflux to generate a vapor, condensing the vapor, contacting the condensed vapor with about 32 kilograms, per kilogram of beclomethasone dipropionate, of a methanol binding agent selected from the group consisting of silica gel or a molecular sieve and returning the condensed vapor to the mixture.

6. The process of claim 5 wherein the methanol binding agent is a molecular sieve.

7. The process of claim 6 wherein the methanol binding agent is a type 3A, type 4A or type 5A molecular sieve.

8. The process of claim 5 wherein the methanol binding agent is a molecular sieve and the process further includes the step of regenerating the molecular sieve that has contacted condensed vapor by heating said molecular sieve to 150° to 200° C. to remove adsorbed methanol.

* * * * *